United States Patent
Baysal et al.

(10) Patent No.: US 11,007,182 B2
(45) Date of Patent: May 18, 2021

(54) USE OF ATPENIN TO ACTIVATE INNATE IMMUNITY

(71) Applicant: Health Research, Inc., Buffalo, NY (US)

(72) Inventors: Bora E. Baysal, Orchard Park, NY (US); Shraddha Sharma, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 537 days.

(21) Appl. No.: 15/564,991

(22) PCT Filed: Apr. 11, 2016

(86) PCT No.: PCT/US2016/026917
§ 371 (c)(1),
(2) Date: Oct. 6, 2017

(87) PCT Pub. No.: WO2016/164889
PCT Pub. Date: Oct. 13, 2016

(65) Prior Publication Data
US 2018/0092889 A1    Apr. 5, 2018

Related U.S. Application Data

(60) Provisional application No. 62/145,057, filed on Apr. 9, 2015.

(51) Int. Cl.
*A61K 31/44* (2006.01)
*A61K 31/4422* (2006.01)
*A61K 38/21* (2006.01)
*A61P 37/02* (2006.01)
*C12N 5/0786* (2010.01)

(52) U.S. Cl.
CPC .......... *A61K 31/44* (2013.01); *A61K 31/4422* (2013.01); *A61K 38/21* (2013.01); *A61K 38/217* (2013.01); *A61P 37/02* (2018.01); *C12N 5/0645* (2013.01)

(58) Field of Classification Search
None
See application file for complete search history.

(56) References Cited

U.S. PATENT DOCUMENTS

2011/0059898 A1    3/2011    Ralph et al.

OTHER PUBLICATIONS

Taggart, R.T., et al., RNA editing of the SDHB transcripts (C to U) in peripheral blood monocytes, ASHG (American Society of Human Genetics) Meeting, 2012, Abstract, 1 page. http://www.ashg.org/2012meeting/abstracts/fulltext/f120120429.htm.
Koning, F.A., et al., Target Cell-Mediated Editing of HIV-1 cDNA by APOBEC3 Proteins in Human Macrophages, Journal of Virology, Dec. 2011, vol. 85, No. 24, pp. 13448-13452.
Paddenberg, R., et al., Essential role of complex II of the respiratory chain in hypoxia-induced ROS generation in the pulmonary vasculature, Am J Physiol Lung Cell Mol Physiol, Jan. 10, 2003, vol. 284, No. 5, pp. L710-719.
Cerecer-Gil, N.Y., et al., Mutation of SDHB is a Cause of Hypoxia-Related High-Altitude Paraganglioma, Clinical Cancer Research, Jun. 30, 2010, vol. 16, No. 16, pp. 4148-4154.
Baysal, B.E., et al., Hypoxia-inducible C-to-U coding RNA editing downregulates SDHB in monocytes, PeerJ., Sep. 10, 2013, vol. 1:e152, 23 pages.
Suspene, R., et al., Somatic hypermutation of human mitochondrial and nuclear DNA by APOBEC3 cytidine deaminases, a pathway for DNA catabolism, Proc. Natl. Acad. Sci. USA, Mar. 22, 2011, vol. 108, No. 12, pp. 4858-4863.
Miyadera, H., et al., Atpenins, potent and specific inhibitors of mitochondrial complex II (succinate-ubiquinone oxidoreductase), Proc. Natl. Acad. Sci. USA, Jan. 21, 2003, vol. 100, No. 2, pp. 473-477.
Baysal, B.E., et al., Oxygen Sensing By Succinate Dehydrogenase Regulates Transcriptional Response to Hypoxia in Monocytes, Dec. 5, 2015, Abstract No. 998, American Society of Hematology, 57th Annual Meeting & Exposition, Section: 201, Granulocytes, Monocytes and Macrophages: Poster I, 3 pages. https://ash.confex.com/ash/2015/webprogram/Paper78859.html.

*Primary Examiner* — Gary B Nickol
*Assistant Examiner* — Jegatheesan Seharaseyon
(74) *Attorney, Agent, or Firm* — Hodgson Russ LLP

(57) ABSTRACT

Provided is a method for inducing innate apolipoprotein B editing catalytic protein (APOBEC) driven C>U RNA deamination of RNA in a cell comprising contacting the cell with an effective amount of atpenin A5 with or without interferon. Specifically, APOBEC3A is a cytidine deaminase enzyme that edits RNA transcripts of hundreds of cellular genes upon stimulation of innate immune cells by low oxygen tension (hypoxia) or antiviral factor interferon. Atpenin A5 induces APOBEC3A-mediated RNA editing in normoxia to levels comparable to those seen in hypoxia. The method can be used to treat viral conditions.

5 Claims, 6 Drawing Sheets

A

B

USE OF ATPENIN TO ACTIVATE INNATE IMMUNITY

CROSS-REFERENCE TO RELATED APPLICATIONS

This application claims priority to U.S. Provisional Application No. 62/145,057, filed on Apr. 9, 2015, the disclosure of which is incorporated herein by reference.

FIELD OF THE DISCLOSURE

This disclosure relates generally to the field of activation of innate immunity and more particularly to inducing innate immunity by activation of apolipoprotein B editing catalytic polypeptide-like (APOBEC) family by atpenin.

BACKGROUND OF THE INVENTION

RNA editing is a co- or post-transcriptional process that alters transcript sequences without any change in the encoding DNA sequence. Although various types of RNA editing have been observed in single cell organisms to mammals, base modifications by deamination of adenine to inosine (A>I), or cytidine to uracil (C>U) are the major types of RNA editing in higher eukaryotes. I and U are read as guanosine (G) and thymine (T) respectively by the cellular machinery during mRNA translation and reverse transcription. RNA editing can therefore alter amino acid sequences, thereby modifying and diversifying protein functions.

The activation-induced deaminase (AID), apolipoprotein B editing catalytic polypeptide-like (APOBEC) family AID causes C>U deamination of DNA. However, multiple studies have failed to identify any RNA editing activity for this protein. Humans have 10 APOBEC genes (APOBEC1, 2, 3A-D, 3F-H and 4). APOBEC3 proteins can deaminate cytidines in single-stranded (ss) DNA, and although the APOBEC proteins bind RNA, C>U deamination of RNA is known for only APOBEC1, with apolipoprotein B (APOB) mRNA as its physiological target$_9$. C>U RNA editing alters hundreds of cytidines in chloroplasts and mitochondria of flowering plants, but the underlying deaminating enzymes are unknown.

APOBEC3A belongs to a family of APOBEC3 enzymes that play an important role in restricting diverse viruses including human immunodeficiency virus (HIV), hepatitis C virus (HCV), hepatitis B virus (HBV) and endogenous retrotransposons. Most studies show that cytidine deaminase catalytic activity of APOBEC3s is essential for their antiviral activities.

SUMMARY OF THE DISCLOSURE

We demonstrate that APOBEC3A is a potent antiviral restriction factor highly expressed in innate immune cells monocytes and macrophages. APOBEC3A is a cytidine deaminase enzyme that edits RNA transcripts of hundreds of cellular genes upon stimulation of innate immune cells by low oxygen tension (hypoxia) or antiviral factor interferon. Thus, biomolecules that activate these enzymes can be used for boosting antiviral immunity. We have identified that hypoxia and interferons activate APOBEC3A-mediated RNA editing in independent and synergistic manners. This disclosure demonstrates that pharmacologic mimics of hypoxia induce APOBEC3A-mediated RNA editing in monocytes and macrophages. We used several cell-permeable compounds. These proteins include atpenin A5 (also referred to herein as atpenin 5) for mitochondrial complex II, DMOG for HIF prolyl hydroxylases and myxothiazol for mitochondrial complex III. We found that atpenin A5 induced APOBEC3A-mediated RNA editing in normoxia to levels comparable to those seen in hypoxia. Similar to hypoxia, atpenin A5 induced RNA editing both independently and synergistically with interferon. In contrast, DMOG and myxothiazol inhibited hypoxia-induced RNA editing. These results suggest that the oxygen sensing process that triggers APOBEC3A-mediated RNA editing in hypoxia occurs in mitochondrial complex II. Based on these results, the present disclosure provides compositions and methods for use as antiviral agents. In one embodiment, the antiviral compositions of the present disclosure are inhibitors of mitochondrial complex II. In one embodiment, the antiviral compositions of the present disclosure boost innate immunity via activation of the APOBEC3A enzyme.

DETAILED DESCRIPTION OF THE INVENTION

Figure 1:
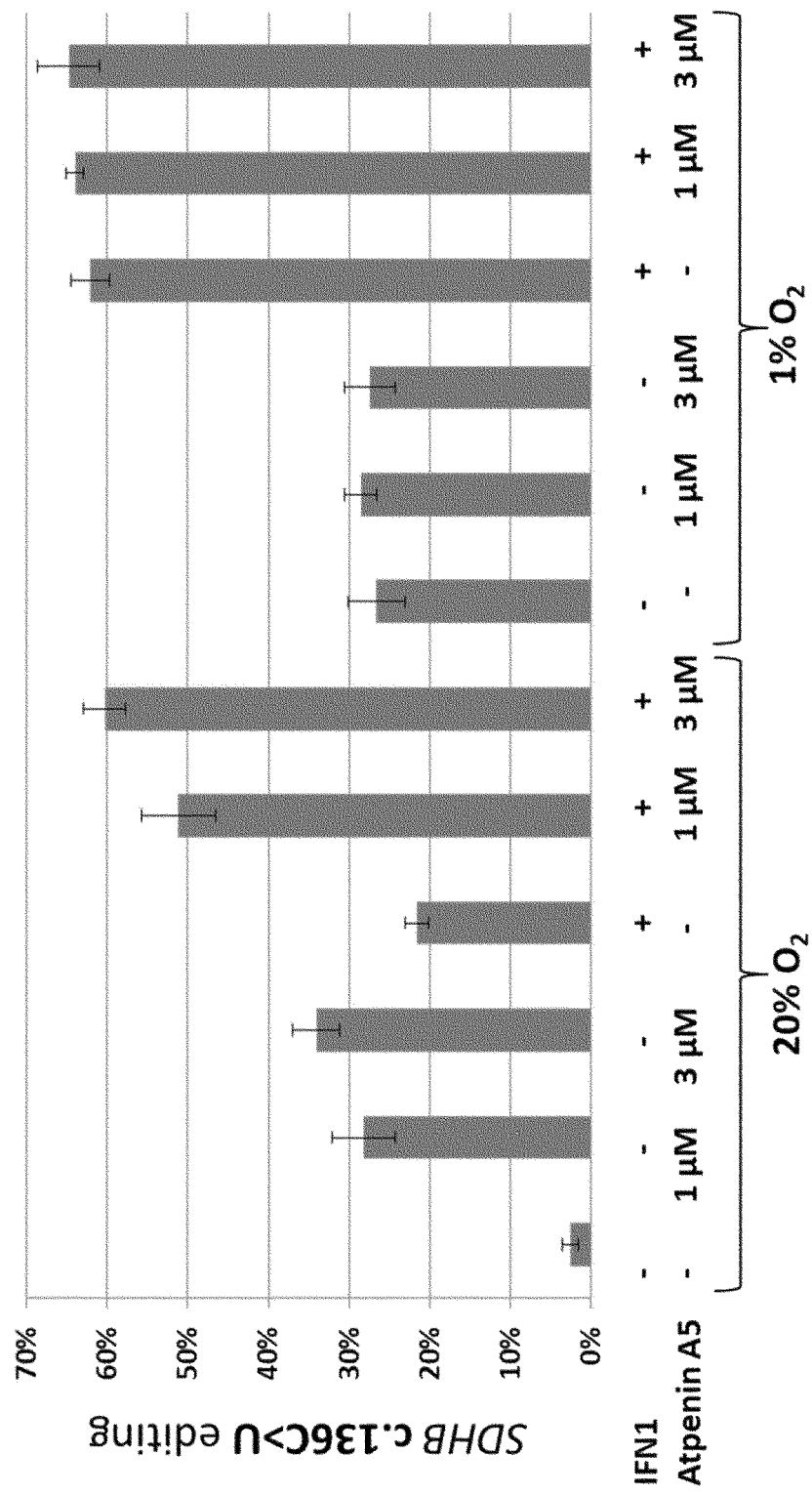
FIG. 1. Atpenin A5 (also referred to herein as AtA5), a complex II inhibitor, induces SDHB site-specific RNA editing in MEPs in normoxia, in both independent and additive manners with interferon type 1 (IFN1). Atpenin A5 does not affect RNA editing rates in hypoxia. Results from 4 biological replicates (mean and SEM).
Figure 2:
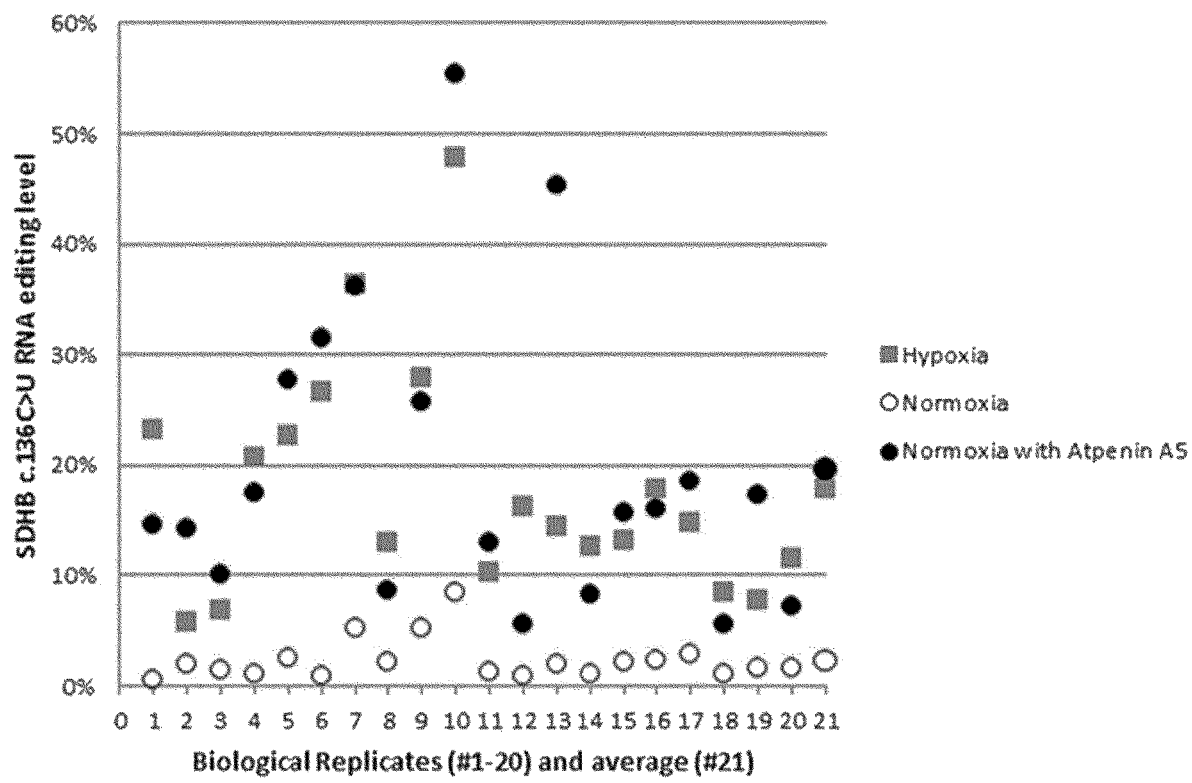
FIG. 2. Effect of atpenin A5 (1-3 micromolar final concentration) in inducing APOBEC3A-mediated RNA editing in normoxia.

The present methods and compositions are based on our observations relating to the effect of hypoxia and interferon on C>U RNA editing. We found that hypoxia (1% $O_2$) enhances the C>U editing of RNA. We also found that transcripts of hundreds of genes including those implicated in viral pathogenesis and Alzheimer's disease are targets of editing in monocytes and macrophages. We show that such editing is regulated by oxygen and interferons (IFN). We further found that APOBEC3A, which belongs to the APOBEC3 family of cytidine deaminases, is an RNA editing enzyme. These findings significantly expand our understanding of C>U RNA editing and open new avenues of inquiry on the role of APOBEC3 genes in viral and chronic diseases.

We demonstrate herein that atpenin A5 induces APOBEC3A-mediated RNA editing in normoxia to levels comparable to those seen in hypoxia. Atpenin A5 is an antifungal antibiotic isolated from *Penicillium* sp. It is commercially available (such as from (Cayman Chemical, Ann Arbor, Mich.) Similar to hypoxia, atpenin A5 induces RNA editing both independently and synergistically with interferon. We found that DMOG and myxothiazol inhibited hypoxia-induced RNA editing. These results indicate that the oxygen sensing process that triggers APOBEC3A-mediated RNA editing in hypoxia occurs in mitochondrial complex II and identify atpenin A5, a specific and highly potent inhibitor of complex II, as an activator of APOBEC3A's catalytic activity.

The present disclosure provides compositions and methods for enhancing RNA editing—in particular, C to U deamination in RNA (referred to herein as "C>U" or "C>U change"). While not intending to be bound by any particular theory, it is considered that the present methods boost innate immunity via activation of the APOBEC3A enzyme.

In one aspect, this disclosure provides a method of inducing C>U deamination in a cell by contacting the cell with a composition comprising one or more interferons. The cells may be isolated, in a tissue, or in an organism. Examples of interferons that are suitable include type 1 interferon (IFN1) and IFNγ.

In one aspect, this disclosure provides a method of enhancing innate C>U deamination by contacting cells with inducers of hypoxia or hypoxia mimicking agents. The cells may be isolated, in a tissue, or in an organism. Hypoxic conditions may be induced by reducing the amount of oxygen that the cells are exposed to. In one embodiment, hypoxia mimicking agents are used. In one embodiment, hypoxia mimicking agents are inhibitors of mitochondrial complex II, such as, for example, atpenin A5.

We observed that when monocyte-enriched PBMCs are treated with atpenin A5 in normoxia (normal oxygen tension), a similar additive effect with interferon is also observed in induction of APOBEC3A catalytic activity. Thus atpenin a5 mimics hypoxia and is a potential antiviral compound that can be used to enhance certain interferon effects.

In one embodiment, the cells are exposed to a combination of hypoxia or hypoxia mimicking agent and interferon.

In one embodiment, this disclosure provides a method of treating a viral infection in an individual by administering to the individual a composition comprising a therapeutically effective amount of an inhibitor of mitochondrial complex II and/or interferon. A composition is considered to be therapeutically effective if it is considered useful for reducing one or more symptoms of the viral infection. Determination of therapeutically effective amounts is within the purview of those skilled in the art. In one embodiment, the individual is a human. In one embodiment, the individual is a non-human animal, such as for example, domestic or farm animals. The phrase "treating" or "treatment" as used herein means reducing the severity of one or more of the symptoms associated with the indication that the treatment is being used for. Thus treatment includes ameliorating one or more symptoms associated with an indication.

Hypoxic conditions for cells in vitro may be created by exposing the cells (such as in a controlled environment chamber, e.g., incubator) to a reduced amount of oxygen compared to atmospheric oxygen. For example, less than 15%, 10%, 5% or 1% oxygen may be used. In one embodiment, the amount of oxygen is from 0.1 to 1%, 0.1 to 5%, 0.1 to 10% and 0.1 to 15% and all percentages there between to the tenth decimal point.

In one embodiment, hypoxic condition or condition that mimic the effects of hypoxia is created by using small molecules that inhibit specific cellular functions. For example, inhibitors of mitochondrial function may be used. In one embodiment, atpenin A5 or other inhibitors of mitochondrial complex II (succinate dehydrogenase) maybe used to mimic hypoxic conditions. Examples of mitochondrial complex II inhibitors also include malonate, diazoxide (DZX), malate and oxaloacetate, 3-nitropropionic acid, nitroxyl, carboxin, TTFA (thenoyltrifluoroacetone). Such agents can therefore, be useful as potential antiviral agents that enhance the C>U cytidine deaminase catalytic activity of APOBEC3A. Thus, these agents may be used in combination with interferons as anti-viral agents via activating APOBEC3A catalytic activity. These agents may be administered in therapeutically effective amounts.

The term "therapeutically effective amount" of a compound refers to an amount which is effective, upon single or multiple dose administration to an individual, for alleviating the symptoms of, or treating the particular indication—either by itself or with a synergistic agent (such as atpenin A5 with interferon). The exact amount desired or required will vary depending on the particular compound or composition used, its mode of administration and the like. Appropriate effective amount can be determined by one of ordinary skill in the art informed by the instant disclosure using only routine experimentation. In one embodiment, the dosage of IFN1 or IFNγ is 5 to 2500 units (and all integer amounts therebetween)/ml. This may be administered via a single or multiple doses or one or more of such dosages may be administered. In one embodiment, the dosage of atpenin A5 is such that the cells are exposed to a concentration of 0.5 μM to 10 μM and all amounts therebetween to the tenth decimal place. In one embodiment, the cells are exposed to 1 μM to 3 μM. The mitochondrial complex II inhibitor and interferon may be administered at the same time or at different times, in the same formulation or different formulations, and by the same route of administration or different routes of administration, The compounds or compositions may be administered as pharmaceutically acceptable salts and may be delivered in pharmaceutically acceptable carriers including liquid or solid filler, diluent, excipient, solvent or encapsulating material, involved in carrying or transporting the subject chemical from one organ, or portion of the body, to another organ, or portion of the body.

Compositions comprising atpenin A5 or atpenin A5 with interferon and a pharmaceutical agent can be can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described can include one or more standard pharmaceutically acceptable carriers. Some examples herein of pharmaceutically acceptable carriers can be found in: *Remington: The Science and Practice of Pharmacy* (2005) 21st Edition, Philadelphia, Pa. Lippincott Williams & Wilkins.

In one embodiment, this disclosure provides compositions comprising atpenin A5, in pharmaceutically acceptable carriers. In one embodiment, interferon is also provided in the composition. The interferon can be IFN1 and/or IFNγ. In one embodiment, kits are provided for use in treatment or amelioration of viral conditions. The kit can comprise separate of combined formulations of atpenin A5 and interferon (such as IFN1 or IFNγ). The kit can also comprise instructions for use of atpenin A5 and/or interferon. The atpenin and/or interferon may be independently formulated (combined or separately) for delivery via any mode, such as for example, intravenous, intramuscular, intraperitoneal, mucosal, dermal, intradermal or any other route.

The present method can be used to induce hypoxia induced gene expression in monocytes. The method can be used to suppress oxygen consumption, but not completely inhibit it. Thus, it can be used as a therapeutic agent, but will not act as a toxin. For example, while atpenin 5 was found to suppress oxygen consumption compared to control, myxothiazol and antimycin were observed to completely inhibit oxygen consumption. Thus, myxothiaxol and antimycin act as toxins while atpenin A5 can be used as a therapeutic agent. The method can be used to suppress HIF-1.

Various methods known to those skilled in the art can be used to administer the compositions of the disclosure to an individual. For example, a compound or mixture of compounds, or compositions containing one or more compound, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intracranial, intradermal, subcutaneous, intraperitoneal, subcutaneous, intramuscular, intrathecal, and intraarticular. The compound(s) also can be administered in the form of an implant, which allows a slow release of the compound(s), as well as a slow controlled i.v. infusion.

Example 1

In this example, we use several cell-permeable compounds which are candidates for oxygen sensing. These inhibitors and the inhibited proteins include atpenin A5 for mitochondrial complex II, DMOG for HIF prolyl hydroxylases and myxothiazol for mitochondrial complex III.

Methods
Isolation and Culture of Cells

Peripheral blood mononuclear cells of anonymous platelet donors were isolated from peripheral blood in Trima Accel™ leukoreduction system chambers (Terumo BCT®, Lakewood, Colo.) after thrombocytapheresis, in accordance with a protocol approved by the institutional review board of Roswell Park Cancer Institute. A density gradient centrifugation method using polysucrose-containing Lymphocyte Separation Medium (Mediatech®, Manassas, Va.) was used for PBMC isolation. MEPs were prepared from PBMCs using the well-established cold aggregation method with slight modification (Mentzer et al 1986). Briefly, PBMCs were subjected to gentle rocking at 4° C. for an hour and aggregated cells that sedimented through fetal bovine serum (FBS; VWR®, Radnor, Pa.) were collected as MEPs (monocyte-enriched PBMCs) after 0.5-3 hours for high monocyte enrichment (~70% monocytes as assessed by immunofluorocytometry for CD14), or after 8-16 hours for mild enrichment (~20%-40% monocytes). MEPs were cultured at a density of at least 20 million per ml in 1 or 2 ml per well of 6- or 12-well standard tissue culture plates under 5% CO2 in RPMI-1640 medium (Mediatech®) with 10% FBS, and 100 U per ml penicillin and 100 μg per ml streptomycin (Mediatech®). CD14 positive monocytes were separated in certain experiments from MEPs that were initially cultured for 1 or 2 days using magnetic beads and donut-shaped magnet (EasySep cell isolation kit purchased from STEMCELL Technologies).

Hypoxia and Interferon Treatments

For hypoxia, cells were cultured under 1% O2, 5% CO2 and 94% N2 in an XVIVO SYSTEM® (a cell culture system) (Biospherix®, Lacona, N.Y.). 'Universal' type I IFN, a hybrid of N-terminal IFNα-2 and C-terminal IFNα-1, produced in *E. coli* were obtained from PBL Assay Science® (Piscataway, N.J.), and respectively used at 300 U per ml. Unless noted otherwise, hypoxia and/or interferon treatments were for 24 hours. Differential viability of MEPs after 1-day culture in normoxia versus hypoxia was not observed as evaluated by Trypan blue stain.

SDHB RNA Editing Assay

SDHB c.136C>U site-specific RNA editing, catalyzed by APOBEC3A cytidine deaminase, was quantified by RT-PCR as described (Baysal et al 2013). Total RNA, genomic DNA and plasmid DNA were isolated using material and methods provided with TRIzol™, DNA Wizard Genomic DNA Purification Kit (Promega®), and Plasmid Kit (Qiagen®, Germantown, Md.), respectively. RNA/DNA was quantified by spectrophotometry on a Nanodrop™ 2000 instrument (Thermo Fisher®). Proteins were quantified using Bio-Rad® Dc™ assay with bovine serum albumin standards. Statistical tests were two-tailed and were performed using R 3.0, Excel™ 2010 (Microsoft®, Redmond, Wash.), or Prism™ 6.0 (GraphPad®, San Diego, Calif.) software.

Cell-Permeable Inhibitors

Atpenin A5 is purchased from Cayman Chemical (CAS 119509-24-9), dissolved in DMSO and used in final concentrations of 1-3 μM in culture. DMOG (dimethyloxalylglycine; CAS 89464-63-1) and myxothiazol (CAS 76706-55-3) are purchased from Sigma-Aldrich, dissolved in DMSO and used in final concentrations of 1 mM and 1 μM, respectively.

Results

We have observed that the innate antiviral restriction factor APOBEC3A modifies the monocyte/macrophage transcriptome by RNA editing in response to pro-inflammatory stimulation by hypoxia and interferons. Because intracellular or viral deamination targets of APOBEC3A could not be previously identified, we considered that APOBEC3A-mediated RNA editing of cellular transcripts is responsible for its antiviral function. Thus, small molecule activators of APOBEC3A-mediated RNA editing may boost antiviral innate immunity.

Hypoxia is a pervasive feature of inflammatory microenvironments. We have shown that hypoxia and interferons act both independently and in synergy to induce APOBEC3A-mediated RNA editing. This finding suggests that mechanisms by which hypoxia and interferon activates APOBEC3A-mediated RNA editing are distinct and collaborative. Hypoxia sensing is mediated by oxygen sensing complexes. Potential candidates for oxygen sensing include HIF prolyl hydroxylases (also known as PhD enzymes), mitochondrial complex III and mitochondrial complex II (succinate dehydrogenase).

To identify the proteins involved in hypoxia-regulated APOBEC3A-mediated RNA editing in monocytes, we used cell permeable inhibitors including DMOG, which inhibits PhD enzymes; atpenin A5, which inhibits mitochondrial complex II and myxothiazol, which inhibits mitochondrial complex III. We found that treatment of monocyte-enriched PBMCs by myxothiazol and DMOG inhibited hypoxia-induced RNA editing and did not induce RNA editing in normoxia (data not shown).

In contrast, atpenin A5 induced APOBEC3A-mediated RNA editing in normoxia without inhibiting the hypoxia-induced RNA editing. We observed normoxic induction of RNA editing by atpenin A5 in 19 of 19 monocyte-enriched PBMCs obtained from anonymous donors (i.e., 19 biological replicates) (p=0.00013, two-sided, Wilcoxon pairwise test). The RNA editing levels induced by atpenin A5 in normoxia were comparable to levels observed upon hypoxic stimulation (FIG. 1). We separated CD14 positive and CD14 negative cell populations from MEPs after culture and confirmed that both hypoxia and atpenin A5 induced RNA editing occurs in CD14+ monocytes. Moreover, atpenin A5 showed a synergistic effect with interferon-induced RNA editing levels. These results indicate that atpenin A5 is a hypoxia mimetic that induces APOBEC3A-mediated RNA editing under normoxia.

Example 2

This example establishes the role of succinate dehydrogenase (mitochondrial complex II) and HIF-1 in regulation of hypoxia-induced gene expression and APOBEC3A-mediated RNA editing in human monocytes.

We used primary human monocytes and 293T HEK cells to investigate their response to hypoxia and to cell-permeable complex II inhibitors (atpenin A5, TTFA) using cell culture methods, high throughout RNA sequencing, qPCR, immunoblotting and oxygen consumption assays.

Figure 3:
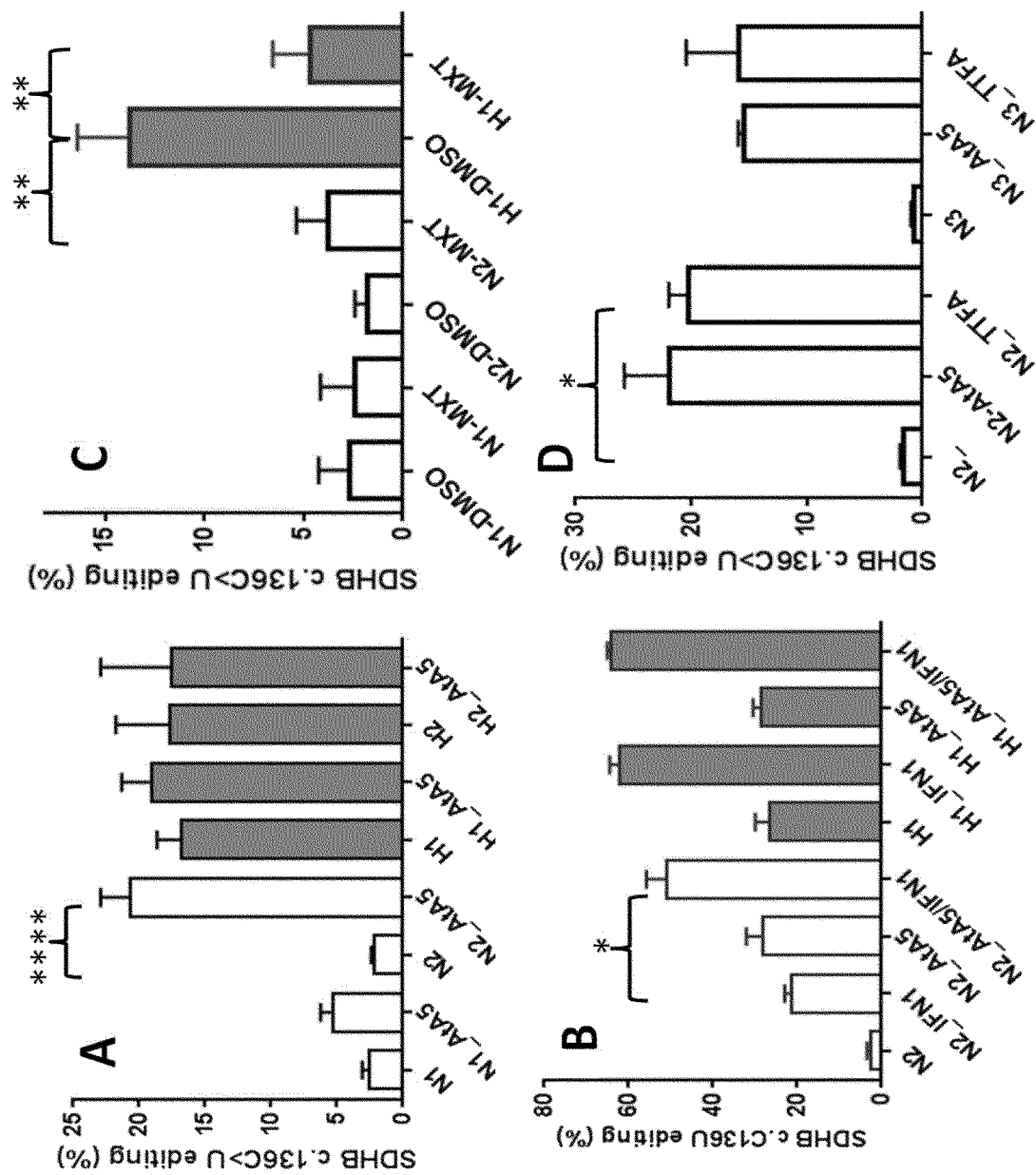
FIG. 3. Inhibition of complex II by AtA5 triggers RNA editing in normoxia. (A) Atpenin A5 (AtA5; 1-2 µM) robustly induces RNA editing in normoxia (N, open bars) in MEPs without interfering with the hypoxic (H, shaded bars, 1% $O_2$) induction (n=27 biological replicates). (B) Similar to hypoxia, AtA5 shows additive effect with interferon type 1 (IFN1) in inducing RNA editing (n=4 biological replicates). (C) Inhibition of complex III by myxothiazol (MXT, 1 µM) does not induce RNA editing in normoxia and inhibits it in hypoxia (n=4 biological replicates). (D) TTFA (1 mM) induces RNA editing in normoxia. Numbers in samples indicate days in culture. Average and SEM are shown. *$P<0.05$, $P<0.01$, **$P<0.0001$ FIG. 4. AtA5 treatment in normoxia induces hypoxic gene expression in monocytes. Heat map shows that the most differentially expressed genes (listed on the right), defined as FDR<0.05, log 2 fold change >3 and average expression >6 cpm, between normoxic control (c1, c2, c3) and hypoxic (1% $O_2$) monocytes (h1, h2, h3) also show similar changes in normoxic monocytes exposed to AA5 (a1, a2, a3).
Figure 4:
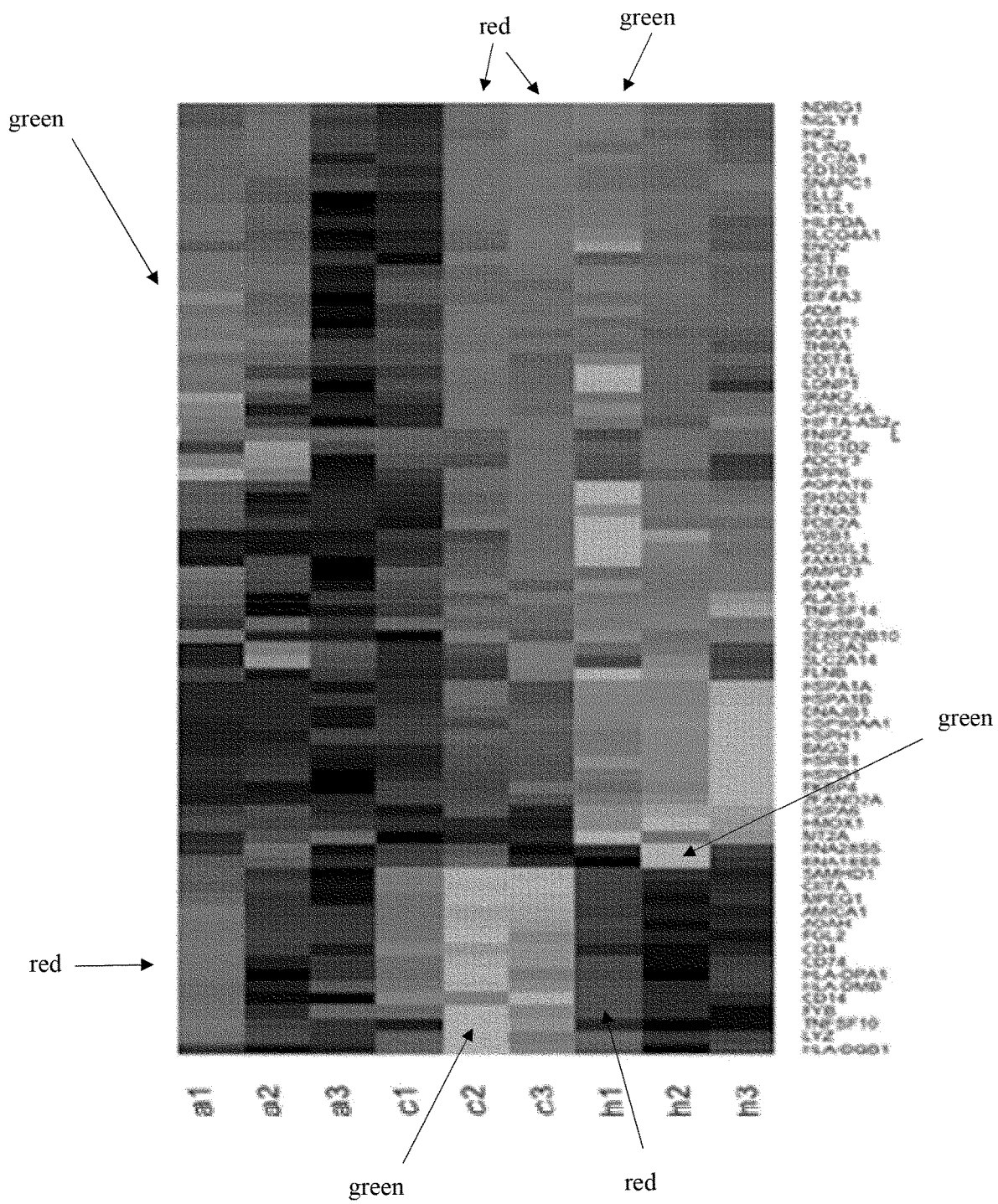
Figure 5:
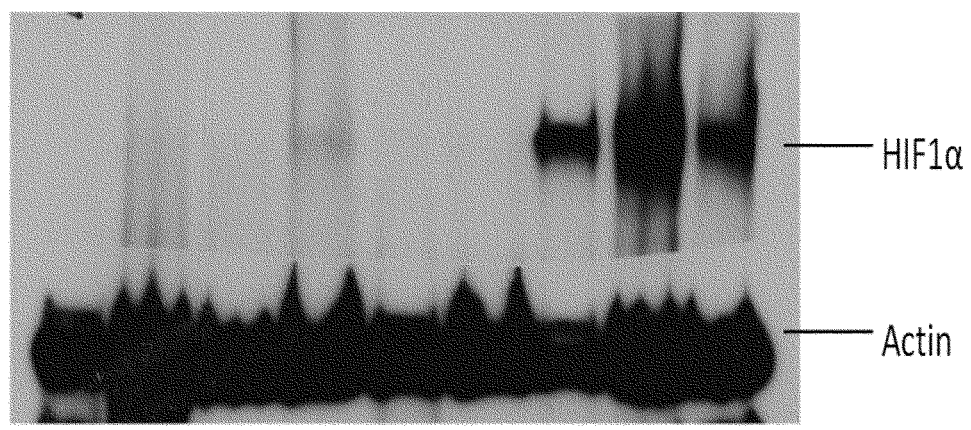
FIG. 5. HIF1α is stabilized in CD14 negative lymphocytes, but not in CD14 positive monocytes in hypoxia (H, 1% $O_2$, day 1). Under normoxia (N), DMOG stabilizes HIF1α in both lymphocytes and monocytes as expected. In contrast, AtA5 does not stabilize HIF1α in normoxia in lymphocytes or monocytes. CD14± cells are unsorted PBMCs.
Figure 6:
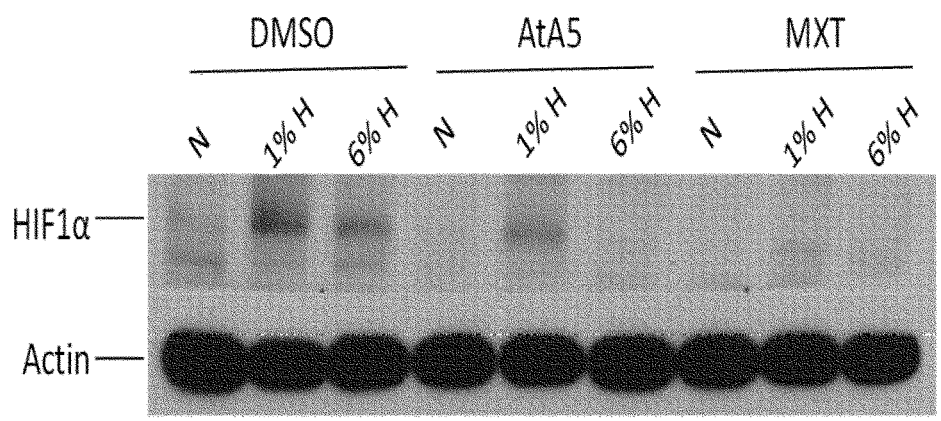
FIG. 6. Inhibition of complex II reduces oxygen consumption and antagonizes HIF-1. (Top)(A) Atpenin A5 (AtA5) inhibits HIF1α stabilization in mild hypoxia (6% $O_2$), whereas myxothiazol (MXT) inhibits it both in mild and severe hypoxia (1% $O_2$) in 293T cells (day 1). DMSO indicates the untreated vehicle control. (Bottom) (B) AtA5 (green) reduces oxygen consumption relative to control cells (blue), but does not abolish it as seen with complex III inhibitors MXT (red) and antimycin A (black). The oxygen levels are measured by a fluorescent dye, which is quenched by oxygen (i.e., more fluorescence, less oxygen). Results are averages from 3 donors' monocyte-enriched PBMCs with SEMs shown in dashed lines.
Figure 6:
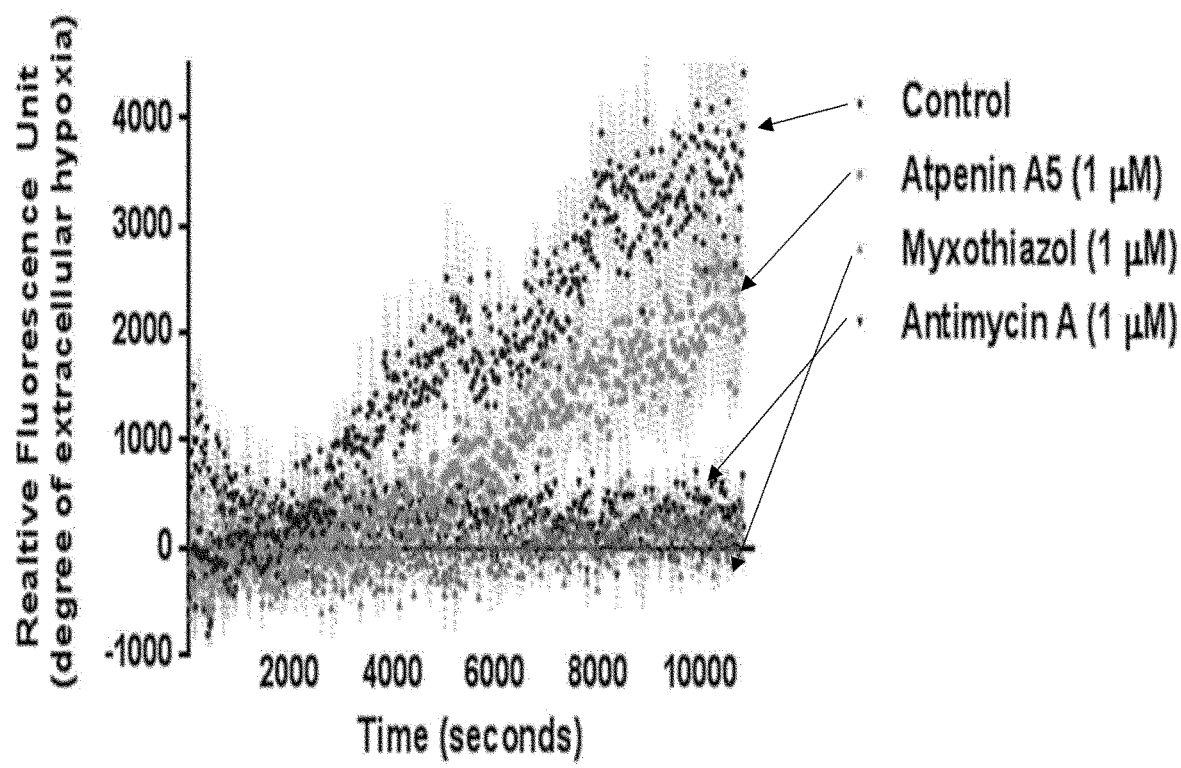

In this example, here we show that inhibition of mitochondrial complex II (succinate dehydrogenase; SDH) by the ubiquinone-analogs atpenin A5 (AtA5) or TTFA induces A3A-mediated RNA editing (FIG. 3) and hypoxic gene expression (FIG. 4) in normoxic cultures of monocytes. RNA seq and RNA editing analyses show that normoxic treatment of monocytes with AtA5 closely mimics the hypoxia effects in inducing transcriptome-scale changes (FIG. 4). RT-qPCR validation experiments confirm that normoxic treatment of monocytes with AA5 induces A3A-mediated RNA editing and causes upregulation of many hypoxia-related and pro-angiogenic genes including VEGFA, CXCL8 (IL8) and CXCR4. AtA5 does not inhibit A3A-mediated RNA editing or transcript induction in hypoxic monocytes. In contrast, myxothiazol, a complex III inhibitor, does not induce A3A-mediated RNA editing in normoxia and inhibits it in hypoxia (FIG. 3). We find that normoxic treatment with AtA5 does not stabilize HIF-1a in monocytes (FIG. 5) or in 293T embryonic kidney cells (FIG. 6). On the contrary, AtA5 reduces cellular oxygen consumption in peripheral blood mononuclear cells and inhibits HIF-1a stabilization in mildly hypoxic conditions in 293T cells (FIG. 6).

This disclosure identifies mitochondrial complex II inhibitor AtA5 as a hypoxia mimetic that induces the hypoxia-related gene expression and RNA editing activity of the antiviral enzyme A3A in monocytes and suggest that oxygen sensing by SDH controls transcriptional responses to hypoxia through a distinct signaling pathway that does not involve HIF-1α.

These data indicate that mitochondrial complex II (succinate dehydrogenase) controls hypoxia-induced transcriptome remodeling in human monocytes through a HIF-independent signaling pathway. Pharmacologic inhibition of complex II by atpenin A5 can provide therapeutic benefit in ischemic conditions by inducing pro-angiogenic gene expression in monocytes.

While the present disclosure contains description of specific embodiments, it will be recognized by those skilled in the art that routine modifications may be made to the compositions, materials, and methods described herein, and such modifications are intended to be within the scope of this disclosure.

What is claimed is:

1. A method of enhancing apolipoprotein B editing catalytic 3A (APOBEC3A) protein driven C>U RNA deamination of RNA in a cell under normoxic conditions comprising contacting the cell with an effective amount of Atpenin A5, wherein the APOBEC3A driven C>U deamination of RNA in the cell is determined to have increased.

2. The method of claim 1, wherein the cell is a monocyte.

3. The method of claim 2, further comprising contacting the cell with an interferon.

4. The method of claim 1, further comprising contacting the cell with an interferon.

5. The method of claim 4, wherein the interferon is IFN1 or IFNγ.

* * * * *